United States Patent [19]
Escher et al.

[11] Patent Number: 4,514,323
[45] Date of Patent: Apr. 30, 1985

[54] UTILIZATION OF 2-HYDROXY-3,4,4-TRIMETHYL-CYCLOPENT-2-EN-1-ONE AS PERFUMING INGREDIENT

[75] Inventors: Sina D. Escher, Le Lignon; Anthony F. Morris, Gingins, both of Switzerland

[73] Assignee: Firmenich SA, Geneva, Switzerland

[21] Appl. No.: 438,315

[22] Filed: Nov. 1, 1982

[30] Foreign Application Priority Data

Nov. 27, 1981 [CH] Switzerland .......................... 7596/81

[51] Int. Cl.$^3$ ....................... C11B 9/00; D06M 13/12; C11D 3/50
[52] U.S. Cl. .................................. 252/522 R; 252/8.6; 252/174.11; 424/69; 424/70; 424/71; 568/379
[58] Field of Search ............... 252/522 R, 8.6, 174.11; 568/379; 424/69, 70, 71

[56] References Cited
PUBLICATIONS

Arctander, Steffen, Perfume and Flavor Chemicals, vol. II, No. 1987, 1969.
Gianturco et al., Tetrahedron, 1963, vol. 19, pp. 2039–2049 and 2051–2059.

Primary Examiner—Thomas A. Waltz
Attorney, Agent, or Firm—Pennie & Edmonds

[57] ABSTRACT

2-Hydroxy-3,4,4-trimethyl-cyclopent-2-en-1-one is used as perfuming ingredient, particularly to reproduce fragrance notes reminiscent of celery and caramel, and aromatic notes of the type of labdanum cistus oil or myrrh.

3 Claims, No Drawings

UTILIZATION OF 2-HYDROXY-3,4,4-TRIMETHYL-CYCLOPENT-2-EN-1-ONE AS PERFUMING INGREDIENT

BRIEF SUMMARY OF THE INVENTION

The instant invention relates to a process to confer to or improve or modify the odorous properties of perfumes and perfumed articles which comprises adding thereto a fragrance effective amount of 2-hydroxy-3,4,4-trimethyl-cyclopent-2-en-1-one.

This invention provides also a perfume composition or a perfume base which contains as active fragrance ingredient 2-hydroxy-3,4,4-trimethylcyclopent-2-en-1-one.

Further, the invention provides a perfumed article containing as active fragrance ingredient 2-hydroxy-3,4,4-trimethyl-cyclopent-2-en-1-one.

BACKGROUND OF THE INVENTION

2-Hydroxy-3,4,4-trimethyl-cyclopent-2-en-1-one, a compound of formula

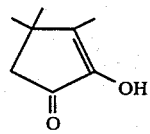

(I)

belongs to the class of derivatives of cyclopentenone, which has been the object of voluminous scientific literature, especially directed to its mono-, di- and tri-methyl-substituted derivatives. Surprisingly, sofar only one of them has raised the perfumer's interest: 2-hydroxy-3-methyl-cyclopent-2-en-1-one has been described in fact as possessing a powerful sweet odor of caramel, spicy character [see S. Arctander, Perfume and Flavor Chemicals, Montclair N.J. 1969; section no. 1987]. Its use in perfumery however remains very limited, its main interest being confined to flavors formulation. Insofar as its dimethyl homologs are concerned, only their utility in the flavor field has been recognized where in fact 2-hydroxy-3,4-dimethyl-cyclopent-2-en-1-one and its corresponding 3,5- and 5,5-dimethyl derivatives are appreciated for their caramel-like, nutty and spicy gustative characters.

The prior art is totally mute about the organoleptic properties of the higher trimethyl homologs, for instance of 2-hydroxy-3,4,4-trimethylcyclopent-2-en-1-one.

We have now surprisingly discovered that this compound possesses useful odorous properties and that consequently it could be utilized very advantageously as perfume ingredient.

PREFERRED EMBODIMENTS OF THE INVENTION

2-Hydroxy-3,4,4-trimethyl-cyclopent-2-en-1-one is characterized by an original odor which can be defined as warm, of celery and caramel type reminiscent of some of the aromatic characters of labdanum cistus oil or myrrh. This powerful scent possesses the property of combining itself harmoniously with a variety of current fragrance notes such as woody, spicy, chypre, animal, oriental or even floral ones. Consequently, 2-hydroxy-3,4,4-trimethyl-cyclopent-2-en-1-one can be used advantageously in the manufacture of perfume compositions or perfume bases destined to fine perfumery as well as to functional products such as cosmetics, soaps, liquid or powder detergents, fabric softeners, household materials, waxes, shampoos or hair lacquers.

Due to its odorous note, warm and spicy at the same time, 2-hydroxy-3,4,4-trimethyl-cyclopent-2-en-1-one can be used for the reconstitution of certain essential oils or resins such as patchouli, foenugreek, myrrh, opoponax or olibanum.

2-Hydroxy-3,4,4-trimethyl-cyclopent-2-en-1-one can be utilized either alone or, more frequently, in solution with current solvents or diluents such as ethyl alcohol, diethyl phthalate, dipropylene-glycol or ethyl-citrate, preferably however in combination with other odorous ingredients such as those currently used in perfumery, e.g. in the manufacture of "coeurs" or base concentrates.

The fragrance effect achieved by the use of 2-hydroxy-3,4,4-trimethyl-cyclopent-2-en-1-one depends inter alia on its concentration and the nature of the coingredients in a given base or composition. For instance, in a typical perfume composition, useful effects can be achieved already by the use of concentrations of the order of 0.01% by weight. The most typical characteristics are obtained by the use of proportions of from about 0.05 to 5% by weight of the given composition. Proportions higher that 5% can also be used, namely whenever special effects are desired.

2-Hydroxy-3,4,4-trimethyl-cyclopent-2-en-1-one is a known chemical that can be synthesized in accordance with the procedure described in the literature [see Gazz. Chim. Ital. 101, 225 (1971)]. The fragrance property of the product thus obtained (m.p. 83°-5°) is perfectly adapted to its above defined use in perfumery.

The following will illustrate but one of the examples of applications of the invention.

EXAMPLE

A perfume base composition of chypre type was prepared by mixing together the following ingredients (parts by weight):

| | |
|---|---:|
| Benjoin Siam | 200 |
| Synth. bergamot oil | 3100 |
| CYCLOSIA ® base[1] | 500 |
| EXALTEX ®[1] | 1000 |
| IRALIA ®[1] | 1500 |
| Abs. oak-moss 50%* | 1000 |
| VERTOFIX ® coeur[2] | 2000 |
| Synth. rose oil | 500 |
| Total | 9800 |

*in diethylphthalate
[1]origin: FIRMENICH SA, Geneva-Switzerland
[2]origin: International Flavors & Fragrances Inc.-New-York, USA By making use of the said Chypre perfume base and of the following three compounds a, b and c, four different compositions were prepared as follows:

Compound a: 2-hydroxy-3-methyl-cyclopent-2-en-1-one [see S. Arctander, op. cit.]
Compound b: 2-hydroxy-3,4-dimethyl-cyclopent-2-en-1-one [see Tetrahedron 19, 2039 (1963)]
Compound c: 2-hydroxy-3,4,4-trimethyl-cyclopent-2-en-1-one.

| Composition | A | B | C | D |
|---|---:|---:|---:|---:|
| Chypre base | 9800 | 9800 | 9800 | 9800 |
| Compound a | 2 | — | — | — |

-continued

| Composition | A | B | C | D |
|---|---|---|---|---|
| Compound b | — | 2 | — | — |
| Compound c | — | — | 2 | — |
| Diethyl phthalate | 198 | 198 | 198 | 200 |
| Total | 10000 | 10000 | 10000 | 10000 |

After dilution to about 10% in 95% ethanol, each of the above mentioned compositions were evaluated by a panel of perfumers. The results of the evaluation can be summarized as follows:

composition A: pleasant odor, not very different from D composition B: the odor effect is more marked, caramel-nutty character; reminiscent of celery, foenugreek; seasoning character composition C: very distinct effect; warm note reminiscent of lovage, myrrh, opoponax and labdanum. Richer and more elegant than D.

What we claim is:

1. Process to confer to or improve or modify the odorous properties of perfumes and perfumed articles which comprises adding thereto a fragrance effective amount of 2-hydroxy-3,4,4-trimethyl-cyclopent-2-en-1-one to impart a warm and spicy odorous note thereto.

2. A perfume composition or a perfume base which contains as active fragrance ingredient from about 0.01% to about 5% by weight of 2-hydroxy-3,4,4-trimethyl-cyclopent-2-en-1-one.

3. A perfumed article containing as active fragrance ingredient from about 0.01% to about 5% by weight of 2-hydroxy-3,4,4-trimethyl-cyclopent-2-en-1-one.

* * * * *